US008936930B2

(12) United States Patent
Arad et al.

(10) Patent No.: US 8,936,930 B2
(45) Date of Patent: Jan. 20, 2015

(54) RED MICROALGAE EXPRESSING EXOGENOUS POLYPEPTIDES AND METHODS OF GENERATING AND UTILIZING SAME

(75) Inventors: Shoshana Arad, Omer (IL); Miri Lapidot, Meitar (IL); Yacob Weinstein, Omer (IL); Ron Dagan, Omer (IL)

(73) Assignees: Ben-Gurion University of the Negev Research and Development Authority, Beer-Sheva (IL); Mor Research Applications Ltd., Tel-Aviv (IL)

(*) Notice: Subject to any disclaimer, the term of this patent is extended or adjusted under 35 U.S.C. 154(b) by 1237 days.

(21) Appl. No.: 11/659,344

(22) PCT Filed: Aug. 4, 2005

(86) PCT No.: PCT/IL2005/000842
§ 371 (c)(1),
(2), (4) Date: Aug. 24, 2007

(87) PCT Pub. No.: WO2006/013572
PCT Pub. Date: Feb. 9, 2006

(65) Prior Publication Data
US 2009/0010947 A1   Jan. 8, 2009

Related U.S. Application Data

(60) Provisional application No. 60/598,849, filed on Aug. 5, 2004.

(51) Int. Cl.
*C12N 1/13* (2006.01)
*C12N 15/79* (2006.01)
*C07K 14/77* (2006.01)
*C12N 15/87* (2006.01)
*C12N 15/09* (2006.01)

(52) U.S. Cl.
CPC .............. *C12N 15/79* (2013.01); *C07K 14/77* (2013.01); *C12N 15/87* (2013.01)
USPC ..................................... 435/257.2; 435/69.1

(58) Field of Classification Search
None
See application file for complete search history.

(56) References Cited

U.S. PATENT DOCUMENTS 5,270,175 A * 12/1993 Moll ................................ 435/41
5,859,346 A *  1/1999 Zhang et al. ................... 800/298
6,027,900 A *  2/2000 Allnutt et al. ................. 435/6.15

FOREIGN PATENT DOCUMENTS

JP      2004-283121     10/2004
WO    WO 2006/013572    2/2006

OTHER PUBLICATIONS

Zhang et al., TAG 107(7) 1157-1168, 2003.*
Sun et al., Biotechnol. Lett. 25:1087-1092, 2003.*
Arad et al., Appl. Environ. Microbiol, 54(10):2411-2414, 1988.*
Lapidot et al. "Stable Chloroplast Transformation of the Unicellular Red Alga Porphyridium Species", Plant Physiology, 129: 7-12, 2002. p. 7, 11.
Walker et al. "Microalgae as Bioreactors", Plant Cell Report, 24: 629-641, 2005.
Communication Pursuant to Article 94(3) EPC Dated Aug. 13, 2009 From the European Patent Office Re.: Application No. 05764347.0.
International Search Report Dated Apr. 21, 2006 From the International Searching Authority Re.: Application No. PCT/IL05/00842.
Response Dated Oct. 28, 2009 to Communication Pursuant to Article 94(3) EPC of Aug. 13, 2009 From the European Patent Office Re.: Application No. 05764347.0.
Supplementary European Search Report and the European Search Opinion Dated Dec. 20, 2007 From the European Patent Office Re.: Application No. 05764347.0.
Written Opinion Dated Apr. 21, 2006 From the International Searching Authority Re.: Application No. PCT/IL05/00842.
Manandhar-Shrestha et al. "The Red Microalgal Cells: A Platform for Recombinant Protein Production", Abstracts/Journal of Biotechnology, 118(Suppl.1): S85, 2005. & 12th European Congress on biotechnology (ECB 12), Copenhagen, Denmark, Aug. 21-24, 2005.
Shrestha et al. "Gene Discovery Through Expressed Sequence Tag (EST) in Porphyridium Sp.: Search for Genes of Industrial and Scientific Importance", Biochemical Society Transactions, 30(1): A29, 2002. & 675th Meeting of the Biochemical Society Joint With the Physiological Society, York, GB, Dec. 18-19, 2001.
Supplemental Response Dated Jul. 22, 2010 to Communication Pursuant to Article 94(3) EPC of Aug. 13, 2009 From the European Patent Office Re.: Application No. 05764347.0.
Sun et al. "Foot-and-Mouth Disease Virus VP1 Protein Fused With Cholera Toxin B Subunit Expressed in *Chlamydomonas reinhardtii* Chloroplast", Biotechnology, 25: 1087-1092, 2003.
Manandhar-Shrestha et al. "The Red Microalgal Cells: A Platform for Recombinant Protein Production", Journal of Biotechnology, XP009093179, 118(Suppl.1): S85, Aug. 2005. & 12th European Congress on Biotechnology (ECB 12), Copenhagen, Denmark, Aug. 21-24, 2005.
Shrestha et al. "Gene Discovery Through Expressed Sequence Tag (EST) in Porphyridium Sp.: Search for Genes of Industrial and Scientific Importance", Biochemical Society Transactions, XP009093182, 30(1): A29, 2002.
Communication Pursuant to Article 94(3) EPC Dated Sep. 9, 2013 From the European Patent Office Re. Application No. 05764347.0.
Sasso et al. "Microalgae in the Postgenomic Era: A Blooming Reservoir for New Natural Products", FEMS Microbiology Reviews, 36(4): 761-785, Jul. 2012.
International Preliminary Report on Patentability Dated Feb. 15, 2007 From the International Bureau of WIPO Re.: Application No. PCT/IL2005/000842.

* cited by examiner

*Primary Examiner* — Nancy T Vogel

(57) ABSTRACT

A method of transforming red microalgae is provided. The method is effected by: (i) culturing red microalgae cells under predetermined light/dilution conditions to thereby generate competent red microalgae cells; and (ii) introducing at least one exogenous polynucleotide into said competent red microalgae cells, thereby transforming the red microalgae.

3 Claims, 11 Drawing Sheets

FIGs 9A-B
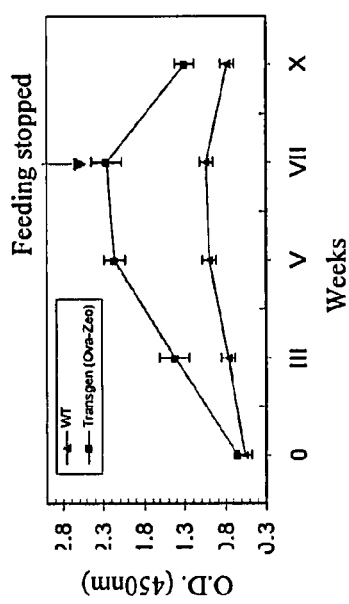
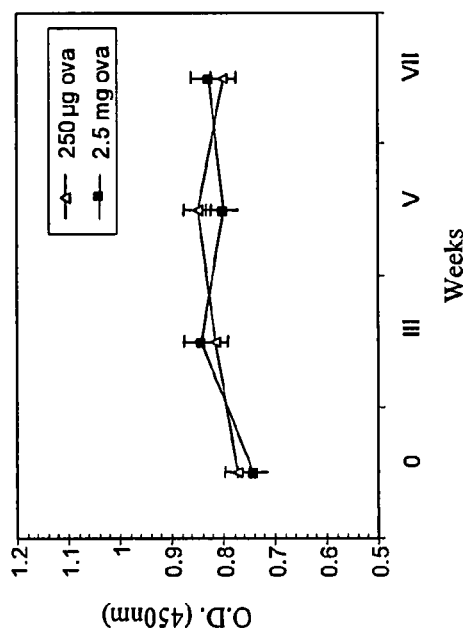

SEQUENCE LISTING

```
<160> NUMBER OF SEQ ID NOS: 17

<210> SEQ ID NO 1
<211> LENGTH: 408
<212> TYPE: DNA
<213> ORGANISM: Streptoalloteichus hindustanus

<400> SEQUENCE: 1
atacgacaag gtgaggaact aaaccatggc caagttgacc agtgccgttc cggtgctcac      60
cgcgcgcgac gtcgccggag cggtcgagtt ctggaccgac cggctcgggt tctcccggga     120
cttcgtggag gacgacttcg ccggtgtggt ccgggacgac gtgaccctgt tcatcagcgc     180
ggtccaggac caggtggtgc cggacaacac cctggcctgg gtgtgggtgc gcggcctgga     240
cgagctgtac gccgagtggt cggaggtcgt gtccacgaac ttccgggacg cctccgggcc     300
ggccatgacc gagatcggcg agcagccgtg ggggcgggag ttcgccctgc gcgacccggc     360
cggcaactgc gtgcacttcg tggccgagga gcaggactga cacggacc                  408

<210> SEQ ID NO 2
<211> LENGTH: 984
<212> TYPE: DNA
<213> ORGANISM: Cauliflower mosaic virus

<400> SEQUENCE: 2
ccgctcacaa ttccacacaa catacgagcc ggaagcataa agtgtaaagc ctggggtgcc      60
taatgagtga gctaactcac attaattgcg ttgcgctcac tgcccgcttt ccagtcggga     120
aacctgtcgt gccagctgca ttaatgaatc ggccaacgcg cggggagagg cggtttgcgt     180
attggctaga gcagcttgcc aacatggtgg agcacgacac tctcgtctac tccaagaata     240
tcaaagatac agtctcagaa gaccaaaggg ctattgagac ttttcaacaa agggtaatat     300
cgggaaacct cctcggattc cattgcccag ctatctgtca cttcatcaaa aggacagtag     360
aaaaggaagg tggcacctac aaatgccatc attgcgataa aggaaaggct atcgttcaag     420
```

```
atgcctctgc cgacagtggt cccaaagatg acccccacc cacgaggagc atcgtggaaa      480
aagaagacgt tccaaccacg tcttcaaagc aagtggattg atgtgataac atggtggagc      540
acgacactct cgtctactcc aagaatatca agatacagt ctcagaagac caaagggcta      600
ttgagacttt tcaacaaagg gtaatatcgg gaaacctcct cggattccat tgcccagcta      660
tctgtcactt catcaaaagg acagtagaaa aggaaggtgg cacctacaaa tgccatcatt      720
gcgataaagg aaaggctatc gttcaagatg cctctgccga cagtggtccc aaagatggac      780
ccccacccac gaggagcatc gtggaaaaag aagacgttcc aaccacgtct tcaaagcaag      840
tggattgatg tgatatctcc actgacgtaa gggatgacgc acaatcccac tatccttcgc      900
aagaccttcc tctatataag gaagttcatt tcatttggag aggacacgct gaaatcacca      960
gtctctctct acaaatctat ctct                                             984
```

```
<210> SEQ ID NO 3
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 3
ccggtcgact ttctccataa taatgtgtga                                       30

<210> SEQ ID NO 4
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 4
ccgctcgagt aattcggggg atctggattt                                       30

<210> SEQ ID NO 5
<211> LENGTH: 185
<212> TYPE: DNA
<213> ORGANISM: Cauliflower mosaic virus

<400> SEQUENCE: 5
tttctccata ataatgtgtg agtagttccc agataaggga attagggttc ctatagggtt      60
tcgctcatgt gttgagcata taagaaaccc ttagtatgta tttgtatttg taaaatactt     120
ctatcaataa aatttctaat tcctaaaacc aaaatccagt actaaaatcc agatcccccg     180
aatta                                                                 185

<210> SEQ ID NO 6
<211> LENGTH: 1234
<212> TYPE: DNA
<213> ORGANISM: Artificial sequence
<220> FEATURE:
<223> OTHER INFORMATION: A nucleic acid construct comprising ovalbumin
      gene

<400> SEQUENCE: 6
gaattcggca tgggctccat cggtgcagca agcatggaat tttgttttga tgtattcaag      60
gagctcaaag tccaccatgc caatgagaac atcttctact gccccattgc catcacgtca     120
gctctagcca tggtatacct gggtgcaaaa gacagcacca ggacacagat aaataaggtt     180
gttcgctttg ataaacttcc aggattcgga gacagtattg aagctcagtg tggcacatct     240
```

```
gtaaacgttc actcttcact tagagacatc ctcaaccaaa tcaccaaacc aaatgatgtt    300
tattcgttca gccttgccag tagactttat gctgaagaga gatacccaat cccgccagaa    360
tacttgcagt gtgtgaagga actgtataga ggaggcttgg aacctatcat ctttcaaaca    420
gctgcagatc aagccagaga gctcatcaat tcctgggtag aatgtcagac aaatggaatt    480
atcagaaatg tccttcagcc aagctccgtg gattctcaaa ctgcaatggt tctggttaat    540
gccattgtct tcaaaggact gtgggagaaa acatttaagg atgaagcaca caagcaatg     600 cctttcagag tgactgagca agaaagcaaa cctgtgcaga tgatgtacca gattggttta    660
tttagagtgg catcaatggc ttctgagaaa atgaagatcc tggagcttcc atttgccagt    720
gggacaatga gcatgttggt gctgttgcct gatgaagtct caggccttga gcagcttgag    780
agtataatca actttgaaaa actgactgaa tggaccagtt ctaatgttat ggaagagagg    840
aagatcaaag tgtacttacc tcgcatgaag atggaggaaa aatacaacct cacatctgtc    900
ttaatggcta tgggcattac tgacgtgttt agctcttcag ccaatctgtc tggcatctcc    960
tcagcagaga gcctgaagat atctcaagct gtccatgcag cacatgcaga atcaatgaa    1020 gcaggcagag aggtggtagg gtcagcagag gctggagtgg atgctgcaag cgtctctgaa   1080
gaatttaggg ctgaccatcc attcctcttc tgtatcaagc acatcgcaac caacgccgtt   1140
ctcttctttg gcagatgtgt ttccccttaa ggcagatgtg gatccactag ttctagagcg   1200
gccgctcgac gatctgtcga tcgacaagct cgag                               1234

<210> SEQ ID NO 7
<211> LENGTH: 681
<212> TYPE: DNA
<213> ORGANISM: Artificial sequence
<220> FEATURE:
<223> OTHER INFORMATION: A nucleic acid construct comprising the gene
      encoding HBsAg

<400> SEQUENCE: 7
atggagaaca tcacatcagg attcctagga cccctgctcg tgttacaggc ggggttttc     60 ttgttgacaa gaatcctcac aataccgcag agtctagact cgtggtggac ttctctcaat   120
tttctagggg gatctcccgt gtgtcttggc caaaattcgc agtccccaac ctccaatcac   180
tcaccaacct cctgtcctcc aatttgtcct ggttatcgct ggatgtgtct gcggcgtttt   240
atcatattcc tcttcatcct gctgctatgc ctcatcttct tattggttct tctgattat    300 caaggtatgt tgcccgtttg tcctctaatt ccaggatcaa caacaaccag tacgggacca   360
tgcaaaacct gcacgactcc tgctcaaggc aactctatgt ttccctcatg ttgctgtaca   420
aaacctacgg atggaaattg cacctgtatt cccatcccat cgtcctgggc tttcgcaaaa   480
tacctatggg agtgggcctc agtccgtttc tcttggctca gtttactagt gccatttgtt   540
cagtggttcg tagggctttc ccccactgtt tggctttcag ctatatggat gatgtggtat   600
tgggggccaa gtctgtacag catcgtgagt ccctttatac cgctgttacc aattttcttt   660
tgtctctggg tatacatttt a                                              681

<210> SEQ ID NO 8
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 8
```
atggagaaca tcacatc                                          17

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
ttaaatgtat acccagagac                                       20

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
ccaagttgac cagtgccgtt cc                                    22

<210> SEQ ID NO 11
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 11
tcggccagga agtgcacgca g                                     21

<210> SEQ ID NO 12
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 12
agaaatgtcc ttcagccaag ctcc                                  24

<210> SEQ ID NO 13
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 13
tcttcagaga cgcttgcagc atcc                                  24

<210> SEQ ID NO 14
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 14
cccaagctta tggagaacat cacatc                                26

<210> SEQ ID NO 15
<211> LENGTH: 29
<212> TYPE: DNA
<213> ORGANISM: Artificial sequence

```
<220> FEATURE:
<223> OTHER INFORMATION: Single strand DNA oligonucleotide

<400> SEQUENCE: 15
ccgctcgagt taaatgtata cccagagac                                        29

<210> SEQ ID NO 16
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 16
atgtcgaagc cagccgtt                                                    18

<210> SEQ ID NO 17
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 17
cggcgcaatc accttgat                                                    18
```

RED MICROALGAE EXPRESSING EXOGENOUS POLYPEPTIDES AND METHODS OF GENERATING AND UTILIZING SAME

RELATED APPLICATIONS

This Application is a National Phase of PCT Patent Application No. PCT/IL2005/000842 having International Filing Date of 4 Aug. 2005, which claims the benefit of U.S. Provisional Patent Application No. 60/598,849 filed on Aug. 5, 2004. The contents of the above Applications are all incorporated herein by reference.

FIELD AND BACKGROUND OF THE INVENTION

The present invention relates to methods of transforming red microalgae and, more particularly, to red microalgae expressing exogenous polypeptides and to methods of producing and utilizing same.

The rapidly growing biotechnology industry is hampered by a limited capacity to produce recombinant polypeptides on a large scale, safely and cost-effectively (Garber, K., Nature Biotechnology 19:184-185, 2001). While manufacturing of recombinant polypeptides can be effected in animal, bacterial, or plant cell systems, each system has major limitations.

Transgenic animal systems are, to date, expensive, require long development timelines and are associated with possible contamination with animal prions and viruses, such as HIV, foot-and-mouth disease, hepatitis etc.

Bacterial systems provide the fastest and easiest way of producing recombinant polypeptides and they are particularly suitable for the synthesis of small and simple molecules, such as insulin and human growth hormone (Goeddel et al., Nature 281:544-548, 1979; Goeddel et al., Proc. Natl. Acad. Sci. USA 76:106-110, 1979; Martial et al., Science 205:602-607, 1979). However, bacterial systems are not suitable for producing complex proteins which tend to fold incorrectly and accumulate as insoluble aggregates (known as inclusion bodies) in bacterial hosts. Several fundamental differences between prokaryotic and eukaryotic organisms account for this phenomenon, including the absence of post-translational protein modification (e.g. glycosylation) in bacteria and the lack of eukaryotic-type chaperone proteins to facilitate correct folding. In addition, production of recombinant polypeptides in bacteria is associated with a risk of endotoxin contamination.

Transgenic plants provide a promising system for producing recombinant polypeptides since they do not carry any infectious agents that are harmful to man, and are highly amenable to scaling up. Thus, in an emerging industry generically known as "molecular farming", genetically modified plants are being used for the production of commercially valuable molecules. Among the applications that are currently being developed in molecular farming are the production of low-cost vaccines and antibodies for therapeutic and diagnostic uses, the production of copious amounts of hormones, cytokines and other bio-active molecules for the treatment of chronic or lethal diseases, the production of bio-safe substitutes for various blood components, the production of degradable plastic biopolymers, the production of unlimited amounts of processing enzymes for the food and pulp industry, the production of low-cost enzymes for waste treatments, and the production of safe bio-active molecules for the cosmetic industry (Daniell et al. Medical molecular farming: production of antibodies, biopharmaceuticals and edible vaccines in plants, Trends Plant Sci. 6:219-226, 2001; Rishi et al. Molecular Farming in Plants: A Current Perspective, J. Plant Biochemistry and Biotechnology 10:1-12, 2001; Mor, et al., Edible vaccines: a concept comes of age, Trends Microbiol. 6:449-453, 1998; and Tacket and Mason A review of oral vaccination with transgenic vegetables, Microbes Infect. 1:777-783, 1999). Yet, recombinant plants growing in open fields pose a serious risk of unintentional release of transgenes to the environment. In addition, the cost of purifying recombinant polypeptides from plant material is presently very high (Schillberg et al., Molecular farming of antibodies in plants. Naturwissenschaften 90: 145-155, 2003).

Red microalgae are attractive prospects for producing recombinant polypeptides since they grow rapidly under closed controlled conditions, pose no danger of unintentional environmental release, have a high vitamin, mineral and unsaturated fatty acid content, while the cell wall polysaccharide comprises antiviral activities (Talyshinsky et al. Cancer Cell International 2: 8, 2000; Huleihel et al., J. Appl. Phycol. 13:127-134, 2001 and U.S. application Ser. No. 10/175,830). In particular, red microalgae are advantageous hosts for producing oral pharmaceutical molecules since they can be used as delivery vehicles of the pharmaceutical molecules. Unlike the rigid microfibrilar cellulose layer typically found in the cell walls of eukaryotic algae, red microalgae cells are encapsulated within a unique complex amorphous polysaccharide (Ramus, J., J. Phycol. 8:97-111, 1972) which provides protection for recombinant polypeptides undergoing an oral route of administration. On the other hand, the unique cell wall composition creates a major obstacle for delivering an exogenous DNA into the red microalgae cells.

U.S. Pat. No. 6,027,900 teaches transforming eukaryotic algae such as *Phaeodactylum tricornutum* by an exogenous DNA which contains the sh ble gene as a selectable marker. However, it does not describe or suggest a procedure which is suitable for transforming red microalgae.

While reducing the present invention to practice, the present inventors have developed a transformation method which is highly suitable for transforming red microalgae. Such a method can be utilized for high throughput, cost effective and safe production of transgenic pharmaceutical and/or nutritive polypeptides and can provide protective encapsulation for their convenient and safe delivery as edible products.

SUMMARY OF THE INVENTION

According to one aspect of the present invention there is provided a method of transforming red microalgae, comprising (i) culturing red microalgae cells under predetermined dilution and light conditions to thereby generate competent red microalgae cells; and (ii) introducing at least one exogenous polynucleotide into the competent red microalgae cells, thereby transforming the red microalgae.

According to another aspect of the present invention there is provided a red microalga cell comprising at least one exogenous polynucleotide.

According to yet another aspect of the present invention there is provided a pharmaceutical composition, comprising at least one red microalga cell expressing at least one exogenous therapeutic polypeptide.

According to still another aspect of the present invention there is provided a food supplement, comprising a red microalga cell expressing at least one exogenous polypeptide having nutritive value.

According to an additional aspect of the present invention there is provided an article of manufacture, comprising a packaging material and transformed red microalgae identified for therapeutic or nutritional use and being contained within the packaging material, the transformed red microalgae expressing at least one exogenous polypeptide having therapeutic or nutritive value.

According to yet an additional aspect of the present invention there is provided a method of producing a polypeptide, comprising (i) culturing red microalgae cells under predetermined dilution and light conditions to thereby generate competent red microalgae cells; (ii) introducing at least one exogenous polynucleotide encoding the polypeptide into the competent red microalgae cells; and (iii) harvesting the polypeptide expressed in red microalgae cells resulting from step (ii).

According to yet an additional aspect of the present invention there is provided a use of a red microalgae cell expressing at least one exogenous therapeutic polypeptide as a pharmaceutical.

According to further features in preferred embodiments of the invention described below, the red microalgae cells are *Porphyridium* species cells.

According to still further features in the described preferred embodiments the method of transforming red microalgae further including, following step (ii), a step of selecting red microalgae cells transformed with the at least one exogenous polynucleotide.

According to still further features in the described preferred embodiments the predetermined light conditions comprise at least 8 hours of continuous darkness.

According to still further features in the described preferred embodiments the predetermined light conditions comprise at least 12 hours of continuous darkness.

According to still further features in the described preferred embodiments the predetermined light conditions comprise at least 16 hours of continuous darkness.

According to still further features in the described preferred embodiments the predetermined light conditions comprise repeated dark/light cycles having a cumulative dark period of at least 8 hours.

According to still further features in the described preferred embodiments the predetermined light conditions comprise repeated dark/light cycles having a cumulative dark period of at least 16 hours.

According to still further features in the described preferred embodiments the predetermined light conditions comprise repeated dark/light cycles having a cumulative dark period of at least 24 hours.

According to still further features in the described preferred embodiments the introducing is effected when the competent red microalgae cells are at a logarithmic growth phase.

According to still further features in the described preferred embodiments the introducing is effected when the competent red microalgae cells are synchronized.

According to still further features in the described preferred embodiments step (i) of the method of transforming red microalgae cells is effected in a culture medium including a concentration of sodium chloride at a concentration ranging between 15 and 35 g/L.

According to still further features in the described preferred embodiments the at least one exogenous polynucleotide includes an antibiotic resistance gene.

According to still further features in the described preferred embodiments the antibiotic resistance gene is zeocin resistance gene.

According to still further features in the described preferred embodiments the Introducing is effected by electroporation.

According to still further features in the described preferred embodiments the introducing is effected by agitation in microparticles.

According to still further features in the described preferred embodiments the microparticles are beads or whiskers.

According to still further features in the described preferred embodiments the step of selecting is effected by culturing the red microalgae cells in a medium comprising a concentration of zeocin or phleomycin capable of inhibiting growth of untransformed microalgae cells.

According to still further features in the described preferred embodiments the at least one exogenous polynucleotide encodes a therapeutic or nutritive polypeptide.

According to still further features in the described preferred embodiments the therapeutic polypeptide is a vaccine.

According to still further features in the described preferred embodiments the therapeutic polypeptide is an oral vaccine.

According to still further features in the described preferred embodiments the exogenous therapeutic polypeptide is a secreted therapeutic polypeptide.

According to still further features in the described preferred embodiments the at least one exogenous polypeptide having therapeutic value is a secreted exogenous polypeptide.

According to still further features in the described preferred embodiments the cell is devoid of an exogenous antibiotic resistance gene.

According to still further features in the described preferred embodiments the oral vaccine is expressed in the red microalgae cells at a level capable of inducing an immunogenic response in a subject upon oral administration.

The present invention successfully addresses the shortcomings of the presently known configurations by providing transformation methods which are highly suitable for transforming red microalgae. In addition, the present invention provides novel transformed red microalgae cells, pharmaceutical compositions, articles of manufacturing and methods of producing polypeptides

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3A and 3B are PCR analyses of total DNA sampled from different transformed algae (lanes 1-15), wild type control (WT) and AlgZeo/35S plasmid containing sh ble gene (P). FIG. 3C is a Southern blot analysis of the electrophoretically separated PCR products obtained from various independent transformed algae (lanes 10-15), wild type control (WT) and plasmid AlgZeo/35S containing sh ble (P), using the sh ble gene as a probe.

FIG. 4A is a PCR analysis using primers against ovalbumin (SEQ ID. NOs: 12 and 13). FIG. 4B is a control PCR analysis using primers against actin (SEQ ID. NOs: 16 and 17). Lanes 1-4, total DNA samples from transformed algae; WT, wild type control; and P, biAlgZeoAlb1 plasmid containing ovalbumin gene.

FIG. 6A is a PCR analysis illustrating presence of an exogenous gene encoding exogenous hepatitis B surface-antigen in transformed cells (lanes 1-4) and its absence in the wild-type control (WT). FIG. 6B is a Western Blot analysis illustrating expression of the exogenous hepatitis B surface-antigen in transformed cultures (lanes 1-5, each lane represents a different culture) and its absence in the wild-type control (WT).

FIGS. 9A-B are ELISA analyses illustrating ovalbumin antibody titer in mouse serum following an eight week period of feeding with transgenic algae expressing ovalbumin or with wild-type algae (control) followed by two additional weeks of regular feeding (FIG. 9A), and ovalbumin antibodies titer in mice fed with pure ovalbumin (FIG. 9B). Each dot represents an average of five mice (replicates).

DESCRIPTION OF THE PREFERRED EMBODIMENTS

Figure 1:
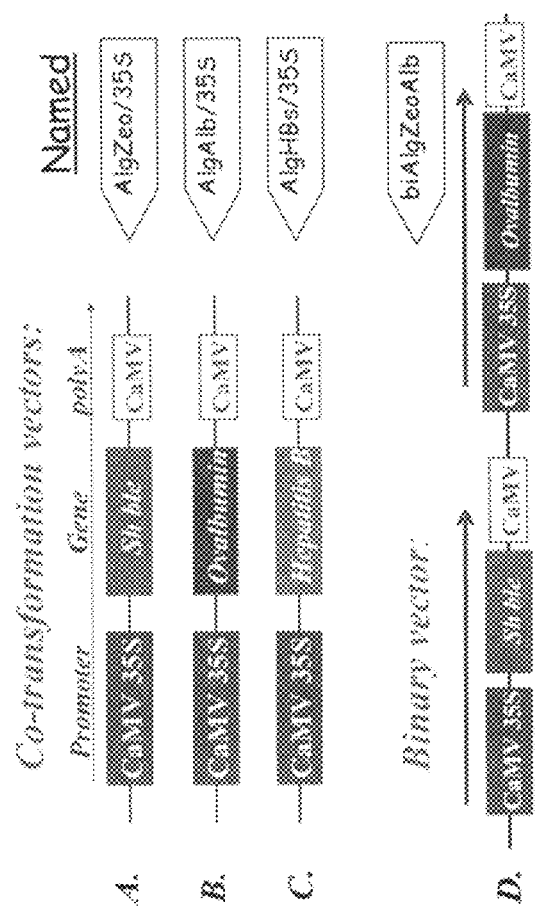
FIGS. 1A-D are schematic illustrations of the nucleic acid constructs of the present invention.
Figure 2:
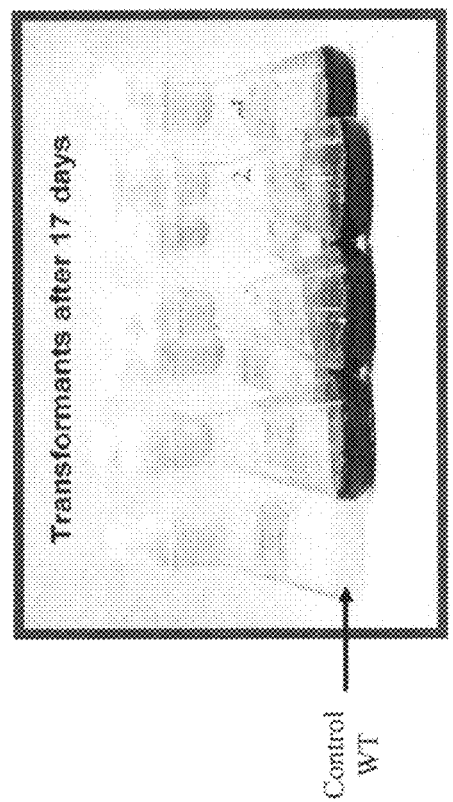
FIG. 2 illustrates cultures of *Porphyridium* sp. transformed with the sh ble gene and a culture of untransformed (wild-type) algae, following 17 days incubation in ASW medium supplemented with zeocin (4 μg/ml). Cultures of transformed algae exhibited growth while no growth of the wild-type control was observed.

The present invention is of methods of transforming red microalgae and of producing exogenous polypeptides in the transformed microalgae cells. Specifically, the present invention can be used to produce recombinant polypeptides in a safe and cost effective manner.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Although methods of transforming eukaryotic algae have been described in the prior art, (see for example, U.S. Pat. No. 6,027,900 which teaches transforming diatom algae), such methods fail to describe or suggest methodology suitable for transforming red microalgae. Such cells are characterized by a unique and complex cell wall which severely limits their capability of acquiring exogenous polynucleotides.

While reducing the present invention to practice, the inventors surprisingly uncovered that cells of *Porphyridium* sp. which had been exposed to continuous light developed a cell wall structure which prevented acquisition of exogenous DNA. Conversely, culturing under appropriate dilution and dark condition allowed *Porphyridium* sp. to readily accept exogenous polynucleotides. Utilizing these unexpected findings, the present inventors generated novel nucleic acid constructs (Example 2), successfully introduced the constructs into competent cells of the red microalga (Example 3), and demonstrated stable integration of exogenous genes and expression in the transformed cells (Example 4). Furthermore, the present inventors demonstrated that cells of *Porphyridium* sp. are capable of secreting recombinant polypeptides (Example 6). In addition, the present inventors also demonstrated that ovalbumin-expressing red microalgae were capable of inducing an immune response in mice upon oral administration (Example 5) suggesting that red microalgae is highly suitable for the production of recombinant polypeptides.

Thus, according to one aspect of the present invention, there is provided a method of transforming red microalgae. The method includes culturing cells under predetermined light conditions for a period of at least 12 hours to thereby generate competent cells, followed by introducing at least one exogenous polynucleotide into the competent cells.

The phrase "red microalgae" used herein refers to any species of red microalgae including, but not limited to, *Porphyridium, Rhodella* and *Rhodosorus* species. The cells of the red microalgae are encapsulated within a complex sulfated polysaccharide (Craig, in: Biology of the red algae 221-257, 1990; Geresh & Arad, Biores. Technol. 38:195-201, 1991).

The red microalgae can be cultured using any conventional culturing approach suitable for culturing of microalgae. Such approaches, one of which is described in EP 576,870 are well known to the ordinary skilled artisan.

The terms "transforming" or "transformation" used herein refer to the introduction of exogenous polynucleotide into cells. As is further described hereinbelow, several methods of transformation can be utilized by the present invention.

As mentioned hereinabove, red microalgae cells require pre-conditioning in order to become transformation-competent. Preparation of transformation-competent red microalgae cells can be effected by continuous culturing in the dark for a period of at least 8 hours, more preferably 12 hours, most preferably 16 hours and ascertaining that the cells reach a logarithmic growth phase. Alternatively, pre-conditioning of red microalgae cells can be effected by culturing the cells under repeated dark/light cycles (having a cumulative dark period of at least 12 hours, more preferably at least 24 hours, most preferably at least 48 hours), as described by Simon-Bercovitch et al. (1999) and ascertaining that the cells are synchronized following the last dark period.

As used herein, the term "exogenous polynucleotide" refers to any nucleic acid sequence which does not naturally occur within the red microalgae and which, encodes an RNA (e.g., siRNA or ribozymes) or polypeptide product expressible in red microalgae. The exogenous polynucleotide of the present invention may encode a soluble (e.g., secreted) or non-soluble polypeptide product.

Since red microalgae are closely related to plants, potentially any plant expressible RNA or polypeptide can be successfully expressed in algae. Plant expressible polypeptides are described in recent reviews of molecular farming including Daniell et al., (Medical molecular farming: production of antibodies, biopharmaceuticals and edible vaccines in plants, Trends Plant Sci. 6:219-226, 2001), Rishi et al. (Molecular Farming in Plants: A Current Perspective, J. Plant Biochemistry and Biotechnology 10:1-12, 2001), Mor, et al. (Edible vaccines: a concept comes of age, Trends Microbiol. 6:449-453, 1998) and Tacket and Mason (A review of oral vaccination with transgenic vegetables, Microbes Infect. 1:777-783, 1999).

Preferably, the exogenous polypeptide is any commercially valuable protein, such as for example polypeptides which are used as pharmaceuticals (therapeutic polypeptides) or as nutraceuticals. The present invention also envisages red microalgae cells expressing more than one recombinant therapeutic or nutritive polypeptide.

The phrase "therapeutic polypeptide" used herein refers to a polypeptide, or peptide which can be used as a medical drug in a human or an animal. Therapeutic polypeptides may be recombinant copies of naturally occurring proteins or mutated and modified versions of naturally occurring proteins. Therapeutic polypeptides include, but not limited to, vaccines, antibodies, hormones, enzymes, anti oncogenic polypeptides, anti diabetic polypeptides and polypeptides which reduce uptake of cholesterol or lower cholesterol blood concentration.

The phrase "nutritive polypeptide" used herein refers to a polypeptide, or peptide which supplies nutrients which may aid in building and toning the body of a human or an animal such as, for example, an antioxidant or a sulfur amino-acid rich protein.

As used herein, the term "vaccine" refers to the active ingredient in a vaccine i.e. the polypeptide portion whose corresponding antibody is elicited in vivo in order to protect against a disease. Vaccines expressed by transgenic plants currently include enterotoxigenic *E. coli* vaccine; *Vibrio cholerae* vaccine; Hepatitis B virus vaccine; Norwalk virus vaccine; Rabies virus vaccine; human cytomegalovirus vaccine; Rabbit hemorrhagic disease virus vaccine; foot-and-mouth disease vaccine; and transmissible gastroenteritis coronavirus vaccine (Daniell et al., Trends Plant Sci. 6:219-226, 2001).

Antibodies expressed by transgenic plants currently include anti glycoprotein B of HSV; anti colon cancer marker antibody; anti *S. mutans* (tooth decay) antibody; Hodgkin's lymphoma ScFv of IgG from mouse; B-cell lymphoma antibody; anti carcinoembryogenic marker ScFV; and anti human creatine kinase. (Rishi et al., J Plant Biochemistry and Biotechnology 10:1-12, 2001).

Other therapeutic polypeptides expressed by transgenic plants currently include human protein C; human hirudin; human granulocyte-macrophage colony-stimulating factor; human somatotropin; human erythropoietin; human enkephalins; human epidermal growth factor; human interferon-alpha; human β-interferon; human serum albumin; human α, β hemoglobin; human homotrimeric collagen; human α-1-antitrypsin; human aprotinin; human lactoferrin; angiotensin-converting enzyme; α-tricosanthin from TMV-U 1; and glucocerebrosidase (Daniell et al., Trends Plant Sci. 6:219-226, 2001).

Enzymes with industrial applications which can be expressed by transgenic plants currently include α-amylase, phytase, manganese peroxidase, β-(1,4) xylanase, canola; β-(1,3) glucanase, barley; and glucuronidase (Rishi et al., J Plant Biochemistry & Biotechnology Vol. 10:1-12, 2001).

In order to enable expression in red microalgae, the exogenous polynucleotide utilized by the present invention is preferably ligated to appropriate regulatory elements to generate a nucleic acid construct (i.e., an expression vector). The regulatory elements (e.g., promoter) are selected to direct transcription of the exogenous polynucleotide in a red microalga host cell.

Any suitable promoter sequence can be incorporated in the nucleic acid construct of the present invention. Such a promoter can be derived from a plant, bacterial, viral, fungal or animal origin. The promoter may be constitutive, i.e., capable of directing high level of gene expression in red microalgae, inducible, i.e., capable of directing gene expression under a stimulus or chimeric.

Preferably, the promoter utilized by the nucleic acid construct is 35S CaMV having the sequence set forth in SEQ ID NO: 2. The nucleic acid construct of the present invention can further include an enhancer, which can be adjacent or distant to the promoter sequence and which functions to up-regulate transcription therefrom.

As mentioned hereinabove, the present invention envisages red microalgae cells expressing more than one recombinant therapeutic or nutritive polypeptide. Various construct schemes can be utilized to express more than one therapeutic or nutritive recombinant polypeptide from a single nucleic acid construct.

For example, two recombinant proteins can be co-transcribed as a polycistronic message from a single promoter sequence of the nucleic acid construct.

To enable co-translation of two recombinant proteins from a single polycistronic message, the first and second polynucleotide segments can be transcriptionally fused via a linker sequence including an internal ribosome entry site (IRES) sequence which enables the translation of the polynucleotide segment downstream of the IRES sequence. In this case, a transcribed polycistronic RNA molecule including the coding sequences of both the first and the second polypeptide will be translated from both the capped 5' end and the internal IRES sequence of the polycistronic RNA molecule to thereby produce both the first and the second recombinant protein.

Alternatively, the first and second polynucleotide segments can be translationally fused via a protease recognition site cleavable by a protease expressed by the red microalgae. In this case, a translated chimeric polypeptide will be cleaved by the red microalgae expressed protease to thereby generate both the first and the second recombinant protein.

Still alternatively, the nucleic acid construct of the present invention can include two promoter sequences each being responsible for expressing a single recombinant protein The nucleic acid construct of the present invention preferably further includes an appropriate selectable marker and/or an origin of replication. A suitable selectable marker can be an antibiotic resistance gene, preferably the sh ble (*Streptoalloteichus hindustanus*) zeocin resistance gene having the sequence set forth in SEQ ID NO: 1.

The nucleic acid construct utilized by the present invention can be a shuttle vector, which can propagate both in *E. coli* (wherein the construct comprises an appropriate selectable marker and origin of replication) and in red microalgae cells. The construct according to the present invention can be, for example, a plasmid, a bacmid, a phagemid, a cosmid, a phage, a virus or an artificial chromosome.

The nucleic acid construct of the present invention can be utilized to stably or transiently transform red microalgal cells. In stable transformation, the nucleic acid molecule of the present invention is integrated into the algal genome and as such it represents a stable and inherited trait. In transient transformation, the nucleic acid molecule is expressed by the transformed cell but it is not integrated into the genome and as such it represents a transient trait.

The nucleic acid construct can be delivered into red microalgae cells using transformation techniques well known in the art including, but not limited to:

(i) biolistic bombardment of cells with DNA-coated microprojectiles (see, for example, in U.S. Pat. No. 6,027,900; Lapidot et al., Plant Physiol. 129: 7-12, 2002; and Klein et al. Bio/Technology 6:559-563, 1988);

(ii) microinjection of DNA directly into cells using very small micropipettes (see, for example, in Neuhaus et al., Theor. Appl. Genet. 75:30-36, 1987; Wu, R., in Plant Biotechnology, Kung, S, and Arntzen, C. J., eds., Butterworth Publishers, Boston, Mass. p. 35-51, 1989; and Neuhaus and Spangenberg, Physiol. Plant. 79:213-217, 1990);

(iii) electroporation by briefly exposing cells to a strong electric field (see, for example in Zhang et al. Plant Cell Rep. 7:379-384, 1988; Fromm et al. Nature 319:791-793, 1986 and in Example 3 hereinbelow); and (iv) agitation of cells with DNA and microparticles (e.g., glass beads or silicon carbide whiskers; see, for example in U.S. Pat. No. 5,464,765; Tuan, R. S. Methods in Molecular Biology Volume 62, Thomas Jefferson University, Philadelphia, Pa., 521 pp., 1997; and in Example 3 hereinbelow).

Preferably, following delivery of nucleic acid constructs into target cells, the transformed red microalgae cells are selected by culturing in a medium supplemented with an antibiotic (e.g., zeocin or phleomycin) at a concentration selected capable of inhibiting growth of untransformed microalgae cells while not affecting growth of transformants which express the zeocin resistance gene sh ble. Preferably, transformed red microalgae cells are cultured in a medium containing at least 3 µg/L zeocin and 15-25 g/L salt (sodium chloride).

As further described below, the transformed red microalgae cells of the present invention can be targeted for human or animal oral consumption. Since genetically-engineered organisms having antibiotic resistance genes are restricted from use in human consumption, any red microalgae cells which are intended for such use must be devoid of any exogenous antibiotic resistance gene, such as sh ble. Thus, preferably, the antibiotic-resistance gene is deleted from any transformed cells which are intended for human consumption. The removal of an antibiotic resistance gene, such as sh ble, from transformed red microalgae can be effected using the bacteriophage Crel lox site-specific recombination system. This consists of two basic components: a recombination enzyme and small DNA recognition sites. These two components are sufficient to perform precisely defined recombination reactions, thereby enabling the removal of specific marker gene (Zhang, et al., TAG 107: 1157-1168, 2003). LoxP is a conserved recombination signal (34 bp) recognized by the Cre recombinase.

The removal of sh ble gene from transformed red microalgae cells may be effected as follows: the loxP sequences are inserted 5' to the promoter of the sh ble gene and 3' to the poly A signal. The Cre gene is then cloned in a similar manner to the sh ble gene 3' to the 35S CaMV promoter to generate an expression vector carrying the loxP sequences. The loxP expression vector is introduced into *Porphyridium* sp. competent cells using the transformation procedure as described in Example 3 of the Examples section hereinbelow and transformed cells expressing a desired foreign gene (e.g., HBsAg) are selected on zeocin-supplemented medium. The selected cells are then transformed with the Cre expression vector and cultured under conditions suitable for recombinase expression which, consequently, results in the deletion of the intervening DNA sequences flanked by loxP. The Cre-transformed cells are then cultured on agar medium not supplemented with zeocin. Transformed red microalgae cells devoid of sh ble gene are subsequently selected using PCR screening confirming the absence of sh ble gene and presence of the foreign gene.

Alternatively, in place of the antibiotic resistance gene, transformed red microalgae cells which are intended for human or animal consumption may include, as a selectable marker, a reporter protein which produces a distinctive fluorescent, luminescent or color signal. Examples of suitable reporter genes include, but not limited to, Green Fluorescent Protein (GFP), luciferase (LUX), β-glucuronidase (GUS) and β.-galactosidase (GAL; Chalfie et al., Science 263: 802, 1994; Jefferson, R. A., Plant Mol. Biol. Rep. 5: 387, 1987; Teeri et al., EMBO J. 8: 343, 1989; Koncz et al., Proc. Natl. Acad. Sci. U.S.A. 84:131, 1987; De Block et al., EMBO J. 3: 1681, 1984).

The transformed red microalgae cells can be cultivated to produce exogenous polypeptides using methods known in the art such as described, for example, in U.S. Pat. Nos. 6,673, 592, 659,977 and. 5,643,585 and EP 576,870. Preferably, the resulting algal biomass is desiccated or freeze-dried, and ground to powder for further use. The exogenous polypeptide may be a secreted polypeptide and consequently the culture medium may be collected and optionally stored for further use.

One particular advantage of producing recombinant polypeptides in red microalgae is the fact that red microalgae cells can be conveniently and safely consumed by both humans and animals and as such no further purification of the exogenous polypeptide is required. In some cases, purification of the recombinant polypeptide from red microalgae may be a disadvantage. For example, in the case of oral administration, the red microalgae cells provide protective encapsulation for convenient and safe delivery. Additionally, in the case of therapeutic polypeptides to be used as vaccines, the cell wall polysaccharide of the red microalgae may comprise built-in adjuvant properties which may be advantageous.

Alternatively, the exogenous polypeptide may require purification prior to use such as to medical grade purity (e.g., >95%). Therapeutic or nutritive polypeptides expressed within the transformed red microalgae can be readily purified therefrom using any one of several well known purification methods. Methods of purification of polypeptides from biomass are described in, for example U.S. patent application Ser. No. 09/925,990 and in Daniell et al., (Medical molecular farming: production of antibodies, biopharmaceuticals and edible vaccines in plants, Trends Plant Sci. 6:219-226, 2001).

It will be appreciated that production of active polypeptides in some cases comprises a sequence of events, commencing with expression of the polypeptide which may be followed by post translational modifications, i.e. glycosylation and possibly proteolytic processing. The glycosylating apparatus in red microalgae as well as the resulting polypeptide glycosylation patterns may not be identical to those in humans. This may increase the recombinant polypeptide's antigenicity and also decrease its half-life.

For some applications this may be of no consequence and even may be of benefit. For example, a non-human glycosylation pattern is not relevant if the recombinant polypeptides are to be delivered orally since the expressed proteins remains in the digestive track and cannot elicit an immune response. The increase in antigenicity may be of benefit if the polypeptides of the present invention are for use as vaccines.

For other applications however, (e.g. non-oral delivery of polypeptides of the present invention, not for use as vaccines) it may be preferable to humanize the glycosylation pattern of recombinant polypeptide products synthesized in red microalgae so that the novel recombinant polypeptides comprise at least in part a human glycosylation pattern.

Koprivova et al (Plant Biology 5, 2003, 582-591) teaches of the molecular cloning of three lower plant moss *Physcomitrella patens* genes involved in the N-glycosylation pathway. Sequence analysis of the moss clones revealed that all three proteins are homologous to their higher plant counterparts. It is therefore expected that other lower plant genes (including red microalgae) will also show homologies to their higher plant counterparts. Thus, molecular cloning of red microalgae genes involved in the N. glycosylation pathway may be performed in a similar way using degenerate primers to conserved domains by one skilled in the art.

In addition to the similarity of the enzymes, the pattern of N-glycans obtained from *P. Patens* was shown to be identical to that of higher plants [Wilson et al., 2001, Biocimica, Biophysica Acta, 1527, 88-96; Koprivova et al., Plant Biology 5, 2003, 582-591]. Therefore, one strategy for the vitro modification of recombinant proteins following their purification may be an alteration of their glycan components by chemical or enzymatic methods (e.g. with glycosidases such as xylosidases or 1,3 fucosidases, or glycosyltransferases such as galactosyltransferase or sialyltransferase).

It will be appreciated that since a preferred method of delivery of the recombinant polypeptides is oral delivery of the red microalgae cells themselves in which the polypeptides are being expressed, the recombinant polypeptides may also be modified whilst they are still inside the red microalgae cells. For example, a particular embodiment of the present invention focuses on modifications of the glycan processing machinery of the red microalgae itself. For example, following the cloning of genes involved in the red microalgae N-glycosylation pathway, anti-sense oligonucleotides capable of inhibiting α-mannosidase I and N-acetylglucosaminyltransferase may be introduced into the transgenic red microalgae of the present invention thus partially blocking red microalga-specific glycosylation. This method has also been adopted for the decrease in plant glycosylation in lower plants such as moss [Koprivova et al., Plant Biology 5, 2003, 582-591; Reski et al, Plant Biotech Journal, 2004, 2 517-523. The recombinant polypeptides would thus partially comprise a mannose-terminated glycan that lack the typical xylose and fucose residues found on plant complex glycans.

Alternatively, the sequence encoding a red microalgae glycosylation site may be modified (provided this does not affect the activity of the recombinant polypeptide) such that glycosylation is prevented.

Yet alternatively or additionally, red microalgae of the present invention may be modified to express human glycan processing enzymes. Palacpac teaches expression of human beta-1,4-galactosyl-transferase in tobacco cells yielding N-linked glycans having a much more "human" composition [Palacpac et al., 96 P.N.A.S. 4692-4697 (1999)] where less than 7% contained xylose and almost 50% comprised terminal galactoses. In a similar fashion human sialyltransferase may be expressed in red microalgae.

Huether et al., [Plant Biology, 2005, May (7) 292-299] teaches generation of transgenic strains of the lower plant moss *Physcomitrella patens* in which the alpha(1,3)-fucosyltransferase and beta(1,2)-xylosyltransferase genes were knocked out by targeted insertion of the human beta(1,4)-galactosyltransferase coding sequence in both of the plant genes (knockin). The transgenics lacked alpha(1,3)-fucose and beta(1,2)-xylose residues, whereas beta(1,4)-galactose residues appeared on protein N-glycans.

Recombinant polypeptides produced from transformed red microalgae cells can be used in therapy per se or as part (active ingredient) of a pharmaceutical composition.

The engineered red microalgae of the present invention may be used as a pharmaceutical (e.g. as a vaccine to protect against a disease or as a therapy to treat a subject in need thereof).

As used herein, the terms "protection" and "protecting" refer to the prevention, amelioration or incidence reduction of infectious organism colonization in the target subject.

As used herein in the specification and claims section that follows the terms "treatment" and "treating" mean alleviation of some or all of the symptoms associated with a disease, prolongation of life expectancy of patients having a disease, as well as complete recovery from a disease.

As used herein, the phrase "subject in need thereof" refers to a mammal, preferably a human.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Preferably, the pharmaceutical composition of the present invention is administered orally. However, suitable routes of administration according to the teaching of the recent invention further include rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. One route of administration which is suited for the pharmaceutical compositions of the present invention is sub-periosteal injection, as described in U.S. Pat. No. 6,525,030 to Erikkson. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate. As used herein, the term "oral administration" includes administration of the pharmaceutical compound to any oral surface, including the tongue, gums, palate, or other buccal surfaces. Addition methods of oral administration include provision of the pharmaceutical composition in a mist, spray or suspension compatible with tissues of the oral surface.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. For example, an effective amount of an oral vaccine means an amount capable of inducing an immunogenic response in a subject upon oral administration.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in an animal model to achieve a desired concentration or titer (see Example 5 hereinbelow). Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in humans or animals. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Exogenous nutritive polypeptides produced in the transformed red microalgae of the present invention can be utilized per se or as a part of a food additive using a suitable carrier such as described hereinabove. Preferably, the food additive is formulated into tablets or placed in gelatin capsules for oral administration. The inventive food supplement formulation may additionally contain a conventional filler and/or extender such as, for example, rice flower.

Therapeutic or nutritive polypeptides produced by the red microalgae of the present invention may be provided per se (or as a part of the pharmaceutical or food additive compositions as described hereinabove). Since red microalgae cells can be conveniently and safely consumed by both humans and animals they may also be administered as a part of the algal biomass produced as described hereinabove.

Hence, the present invention provides a method of transforming red microalgae which can be utilized to produce valuable polypeptides reliably, safely, and cost effectively.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Antibiotic Sensitivities of *Porphyridium* Sp.

*Porphyridium* sp. (UTEX 637, from the culture collection of algae at the University of Texas at Austin) cells were cultured in artificial seawater (ASW; Jones et al. Plant Physiol. 16:636-643, 1963) supplemented with different antibiotic compounds for evaluating antibiotic sensitivities. As can be seen in Table 1, *Porphyridium* sp. was insensitive to most of the common antibiotics for which resistance genes are available, while exhibiting no growth when exposed to zeocin at a concentration of 4-8 μg/ml.

TABLE 1

Effect of different antibiotics on *Porphyridium* sp. growth

| Compound | Concentration (μg/ml) | Growth[1] |
|---|---|---|
| Paramomycin | 200 | ++ |
| Neomycin | 150 | ++ |
| G418 | 2 | + |
| Phleomycin | 10 | ++ |
| Hygromycin | 1 | ++ |
| Lincomycin | 300 | ++ |
| Chloramphenicol | 200 | + |
| Chloramphenicol | 500 | − |
| Spectinomycin | 300 | ++ |
| Kanamycin | 700 | ++ |
| Methotrexate | 80 | ++ |
| Cyclohexhimide | 5 μM | − |
| Zeocin | 4-8 | −− |

[1]++, no inhibition of growth rate.
+, slight inhibition of growth rate.
−, no growth.

Example 2

Nucleic Acid Constructs

Zeocin-Resistance Construct:

A 408 bp polynucleotide fragment comprising the Sh ble gene, set forth in SEQ ID NO: 1, was cut with AflIII from plasmid pEF4/His-B (Invitrogen USA), blunt-ended by klenow and inserted into the HincII site of cloning vector KSII (Bluescript), that was previously adapted by inserting a SalI site into the EcoRV site of the KSII vector.

The 35S-CaMV-x2 promoter fragment (SEQ ID NO:2) was cut with XhoI and SalI from plasmid 1305.1 (Cambia, Australia), and inserted into the SalI site of the KSII-Sh ble construct (at the 5'-end of the Sh ble gene) to generate the S35ZeoKSII plasmid.

The CaMV polyA fragment (pA2; SEQ ID NO: 5) was amplified from the plasmid 1305.1 (Cambia) by PCR using the primers set forth in SEQ ID NOs: 3-4 which created XhoI and SalI sites at the 5' and 3' end regions of the reading frame, respectively. The PCR product was subcloned into pGEMT-Easy plasmid (Promega, USA) to generate the pGEMT-pA2 plasmid. The S35-Zeo region was removed from the S35ZeoKSII by XhoI and SalI cutting and inserted into the Sal I site of the pGEMT-pA2 plasmid (at the at the 3' end of the Sh ble gene) to generate the AlgZeo/35S vector.

The resulting zeocin-resistance construct comprised the Sh ble gene flanked by a 35S promoter and polyA adenylation sequence (FIG. 1A).

Ovalbumin Construct:

A nucleic acid construct comprising ovalbumin gene (SEQ ID NO: 6) flanked by a 35S promoter and polyA adenylation sequence (FIG. 1B) was constructed by replacing the Sh ble gene in the zeocin construct described above with the ovalbumin gene, as follows:

Ovalbumin encoding cDNA was removed from the plasmid pcDNA3 by cutting with restriction enzymes EcoRI and XhoI. The fragment was blunt ended by klenow and ligated into the HindIII site of the plasmid KSII (Bluescript). A 1161 bp fragment encoding ovalbumin (See above) was cut from the plasmid with HindIII and XhoI and was inserted into the HindIII-XhoI site of the zeocin construct (thereby replacing the Sh ble gene) to generate the AlgAlb/35S vector.

Hepatitis B Surface-Antigen Construct (HBsAg):

A nucleic acid construct comprising the gene encoding HBsAg (SEQ ID NO: 7) flanked by a 35S promoter and polyA adenylation sequence (FIG. 1C) was constructed by replacing the Sh ble gene in the zeocin construct described above, with the HBsAg gene (FIG. 1C), as follows:

The gene encoding HBsAg was amplified from the plasmid pSVHBV (Dr. Y. Shemer, Ben-Gurion University) by PCR using the primers set forth in SEQ ID NOs: 8-9 which created restriction sites of HindIII and XhoI at the 5' and 3' ends regions of the reading frame, respectively. The PCR product was then inserted into the HindIII-XhoI site of the zeocin construct (thereby replacing the Sh ble gene), to generate the AlgHBs/35S vector.

Binary Construct Carrying Genes Encoding Sh Ble and Ovalbumin:

A nucleic acid construct comprising the Sh ble gene flanked by a 35S promoter and polyA adenylation sequence and the Ovalbumin gene flanked by a 35S promoter and polyA adenylation sequence (FIG. 1D) was constructed as follows:

A 2.3-kb fragment, containing the 35S promoter and the ovalbumin gene was cut from the ovalbumin construct described above with XhoI and SalI restriction enzymes and inserted into the SalI site of the plasmid pGEM-Teasy containing the PCR fragment the polyA sequence described above, to produce a plasmid comprising the ovalbumin gene flanked by the 35S promoter and the polyA sequence.

The polynucleotide fragment containing the ovalbumin gene flanked by the 35S promoter and the polyA sequence was removed from the plasmid by cutting with SalI-XhoI and was inserted into the SalI site of the zeocin construct described above to generate the binary construct named biAlgZeoAlb 1.

Example 3

Transformation of Red Microalgae

Materials and Methods:

Generating competent cells: *Porphyridium* sp. (UTEX 637, from The culture collection of algae at the University of Texas at Austin) cells were cultured in 250 ml flasks containing artificial seawater (ASW; Jones et al. Plant Physiol. 16:636-643, 1963) with continuous shaking (100-120 rpm) under a continuous light supplied from above (90 μmol photons/m$^2$) at 25° C. for 48 hr. The algal culture was then diluted to a density of about $4 \times 10^6$ cells/ml followed by an additional incubation of 48 hr under the same conditions. This process was repeated 3-4 times in order to generate a fresh fast growing "starter culture". The starter culture was then divided into three parts for additional incubation under the following conditions:

(i) Under continuous light for 24-48 hr (logarithmic phase cells).
(ii) In the dark for 16 hr (logarithmic phase cells).
(iii) Under 4 cycles of dark-light-dilution regime according to the procedure described by Simon-Bercovitch et al. (1999; Cell-wall formation during the cell cycle of *Porphyridium* sp. (Rhodophyta). *J. Phycol.* 35 78-83.).

Transformation of red microalgae cells: Competent red microalgae cells were transformed with the following nucleic acid constructs (described in Example 2 above), or combinations of constructs, as follows:

(i) zeocin-resistance construct only.
(ii) binary zeocin-resistance and ovalbumin construct only.
(iii) zeocin-resistance construct combined with ovalbumin construct.
(iv) zeocin-resistance construct combined with HBsAg construct.

The nucleic acid constructs were delivered as circular or linear plasmids (3 μg plasmid/transformation) to competent algal cells using two of the following delivery methods:

(i) Agitation of 300 μl algal culture ($1 \times 10^7$ cell/ml) for 20 sec with 0.3 g glass beads (0.4-0.6 μm).

(ii) Electroporation of 250 μl algal culture volume ($1 \times 10^8$ cells) at 1900-2400 V/cm and a capacitance of 10 μF using a gene pulser cuvette of 4 mm electrode gap.

The treated cells were spread over ASW agar (1.5%) supplemented with zeocin (3 μg/ml), or were added to liquid ASW supplemented with zeocin (4 μg/ml). The cultures were incubated at 25° C. for 10-21 days under a continuous light regime (90 mmol photons/m$^2$) and agitation (liquid culture only) to enable selective regeneration of transformed cells.

Results:

Zeocin resistance (transformed) cells developed on both solid and liquid selective media. Transformed cells were generated with all nucleic acid construct combinations (zeocin-resistance construct only; binary zeocin-resistance and ovalbumin construct only; zeocin-resistance construct combined with ovalbumin construct; and zeocin-resistance construct combined with HBsAg construct). However, transformed cells were obtained only when circular constructs (plasmids) were used and were not obtained when linear constructs were used. Transformations were especially successful using the glass bead agitation procedure.

Surprisingly, transformation was effected only when logarithmic algal cells had been pre-conditioned by incubation in the dark for 16 hr, or by incubation under dark-light cycles, prior to exposure to exogenous DNA. In contrast, transformation of red microalgae cells which had been kept under continuous light was substantially ineffective. Thus, the results clearly indicate that transformation of red microalgae uniquely require a prior exposure to a period of darkness.

Example 4

Expression of Exogenous Genes in Transformed Red Microalgae

Materials and Methods:

Extraction of DNA: Total DNA was extracted from transformed and wild type algae using the CTAB method as described in Patwary & van der Meer. (*J. Phcol.* 30:91-7, 1994).

PCR Analysis: Sh ble and ovalbumin genes were amplified from DNA extracts by PCR using the primers set for in SEQ ID NOs: 10-11 (for Sh ble) and SEQ ID NOs: 12-13 (for ovalbumin gene) using the following PCR protocol: 3 cycles of: 95° C.—2 min, 61° C.—1 min, 72° C.—1 min, following by 30 cycles of: 95° C.—30 sec, 63° C.—45 sec, 72° C.—1 min, ending with 72° C.—5 min and cooling to 4° C.

Southern blot analysis: The identity of the sh ble PCR products were verified by hybridizing the electrophoresis-separated PCR products with a sh ble coding-sequence probe using standard Southern blotting procedures (Sambrook, J. et al., Molecular Cloning: A Laboratory Manual. Cold Spring Harbor Laboratory Press, 1989).

Protein extraction: Total proteins were extracted by performing 4 cycles of freeze-thawing of $90 \times 10^6$ algal cells in 200 μl of PBS containing 3% βME. The homogenates were centrifuged at 14,000 g for 15 min. A small aliquot of each supernatant was than reserved for protein determination by the Bradford method. The remaining supernatants were used for determination of foreign protein expression levels by Western blot analysis.

Western blot analysis: The expression level of the foreign proteins in algal transformants was tested using a standard Western blot immunoassay with the polyclonal antibody against Sh ble (Cayla, USA) and monoclonal antibody against ovalbumin (Sigma). The antibodies were diluted as recommended, 1:500 for sh ble and 2:500 for ovalbumin.

Figure 3:
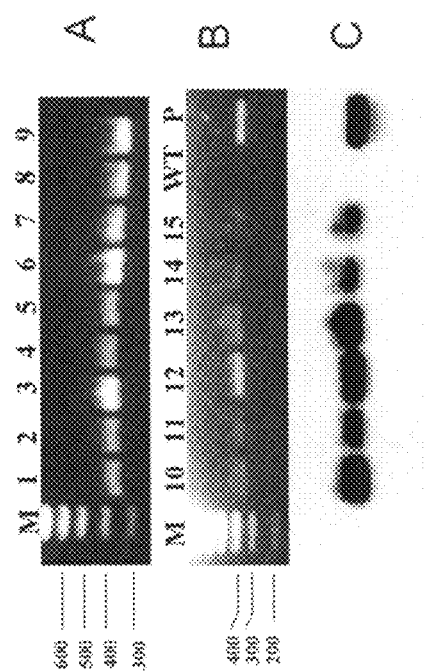
FIGS. 3A-C illustrate presence of sh ble gene in transformed *Porphyridium* sp.

Results:

Presence and expression of exogenous Sh ble protein: Presence of Sh ble gene in DNA of transformed algae was confirmed by PCR analysis (FIG. 3A) as well as by Southern blot analysis (FIG. 3B). The Sh ble gene was not detected in the wild type control.

Figure 5:
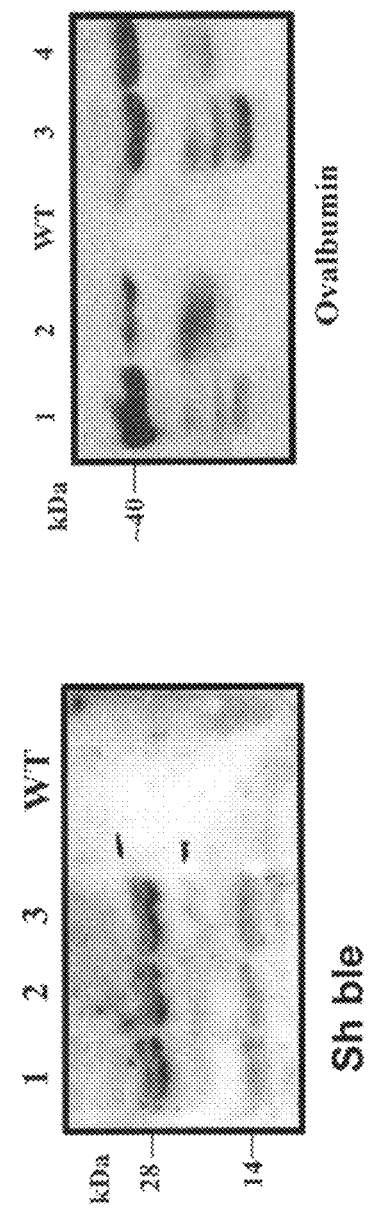
FIGS. 5A-B are Western blot analyses illustrating expression of exogenous Sh ble (FIG. 5A, lanes 1-3) and ovalbumin (FIG. 5B, lanes 1-4) proteins in transformed *Porphyridium* sp. and their absence in the wild type control (WT).

Expression of Sh ble protein in transformed algae was confirmed by Western blot analysis (FIG. 5A). The Sh ble protein was not detected in the wild type control.

Figure 7:
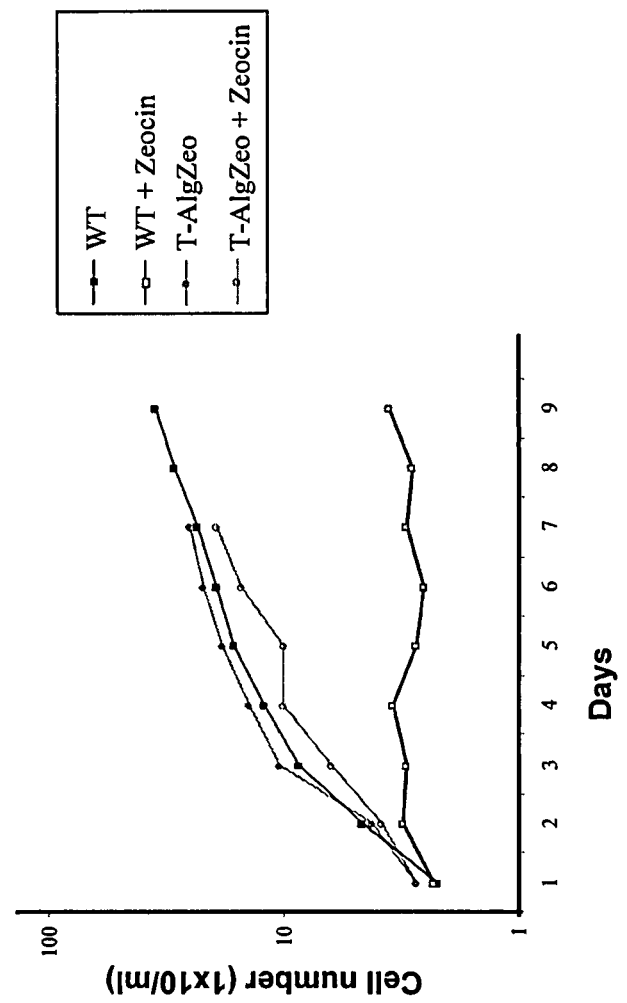
FIG. 7 illustrates growth rates of cultured transformed and wild-type *Porphyridium* sp in a presence or absence of 10 μg/ml zeocin

As can be seen in FIG. 7, only transformed algae which carried the Sh ble gene were capable of growing in the presence of zeocin (10 μg/ml), whereas no growth of wild type algae was observed in the presence of zeocin.

Figure 4:
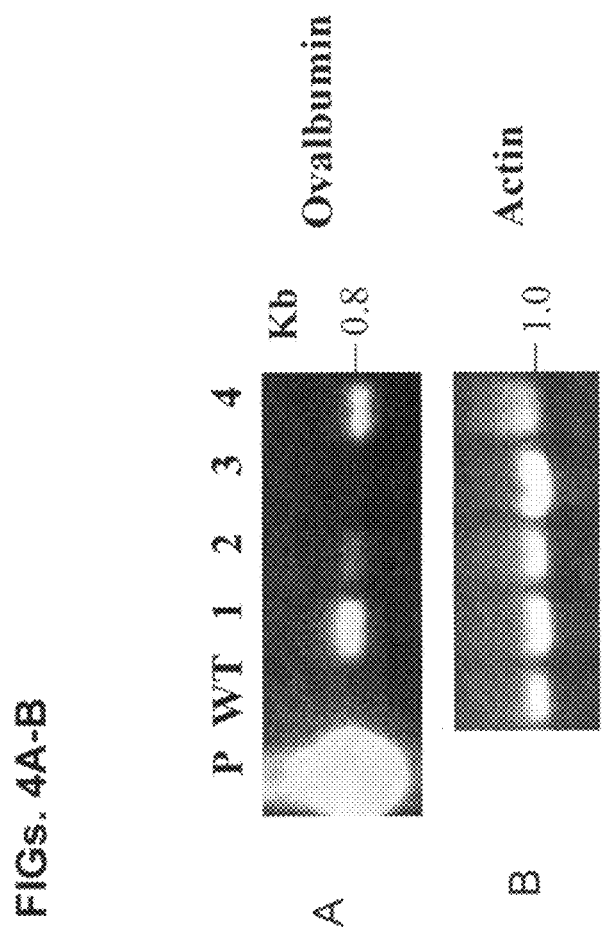
FIGS. 4A-B are PCR analyses illustrating presence of ovalbumin gene in transformed *Porphyridium* sp.

Presence and expression of exogenous ovalbumin protein: Presence of the ovalbumin gene in genomes of algae which were transformed with a binary construct carrying both Sh ble and ovalbumin genes, was confirmed by PCR analysis (FIG. 4). The ovalbumin gene was not detected in the wild type control.

Expression of ovalbumin in transformed algae was confirmed by Western blot analysis (FIG. 5B). Ovalbumin was not detected in the wild type control.

Figure 8:
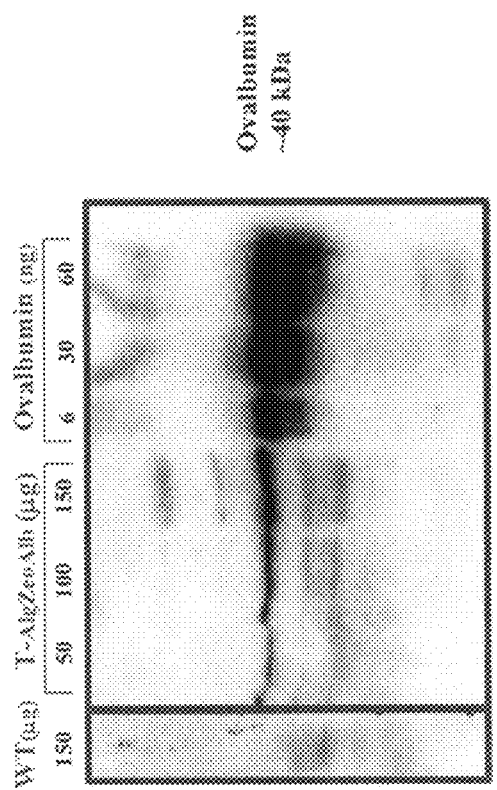
FIG. 8 is a Western blot analysis illustrating expression levels of ovalbumin present in different amounts of crude protein obtained from transformed *Porphyridium* sp., in comparison with increasing amounts of pure ovalbumin.

The level of ovalbumin expression in transformed red microalgae was estimated by visually comparing Western blot intensities of different amounts of protein extracts (obtained from ovalbumin-transformed algae) to blot intensities of different amounts of pure ovalbumin (FIG. 8). It was thus estimated that 100 μg of protein extract (obtained from about $10^7$ transformed algal cells) contained about 6 ng ovalbumin. Accordingly, one liter of culture containing $40 \times 10^9$ cells/ml (about 4-6 g biomass) can generate 45-90 μg ovalbumin.

Figure 6:
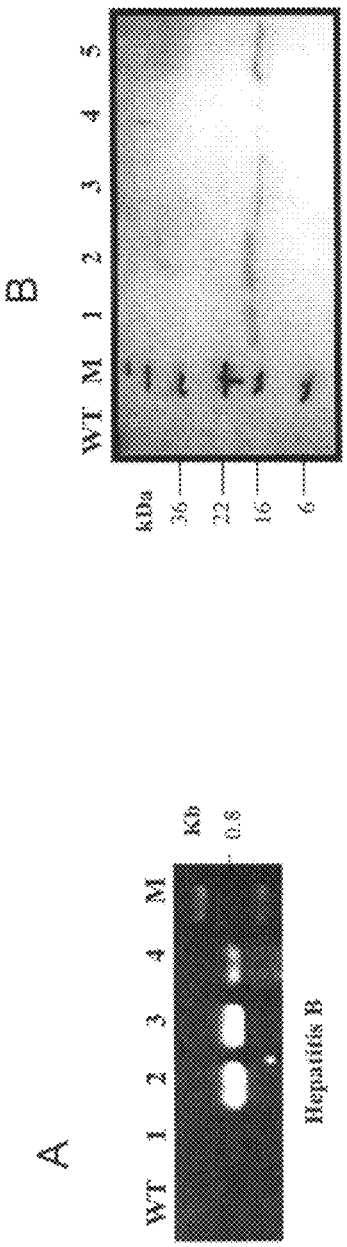
FIGS. 6A-B illustrate expression of exogenous hepatitis B surface-antigen in transformed *Porphyridium* sp.

Hepatitis B gene expression: The presence of the HBsAg gene in DNA of transformed algae, obtained by co-transformation with the zeocin and HBsAg constructs, was shown by PCR analysis (FIG. 6A). Expression of HBsAg in transformed algae was confirmed by Western blot analysis (FIG. 6B). The HBsAg gene was not detected in the wild type control.

Example 5

Use of Ovalbumin-Transformed Red Microalgae as an Oral Vaccine

Materials and Methods:

Algal biomass: transgenic red microalgae expressing ovalbumin were generated as described in Examples 2-3 above. Biomass samples of transformed and wild-type red microalgae were lyophilized and gently ground to powder leaving most of the cells intact.

Animal feeding with algal biomass: Five week old Balb/C mice were fed with dry biomass powder of transgenic or wild-type algae. Each group included five mice (replications). Each mouse was fed with a mixture of 2.5 g of algal biomass powder (containing ~37.5 μg ovalbumin) and 2.5 g of ground regular mouse food, for two days per week over a period of five weeks. Two additional control groups of two mice each were fed with 250 μg or 2.5 mg purified ovalbumin. Blood was drawn from all mice on day 0 and at the end of each week, for evaluation of anti-ovalbumin antibody titer by ELISA.

ELISA evaluation of total anti-ovalbumin antibody titer in mouse serum: Microtiter plates (Maxi-Sorp; Nunc A S, Roskilde, Denmark) were coated with ovalbumin (Sigma A 2512) by adding 50 µl aliquots of ovalbumin suspension (40 µg ovalbumin per ml PBS) to all wells. The plates were incubated at 37° C. for 1.5 hr, following which the liquid was removed by aspiration and then re-filled with a blocking solution [10% foetal calf serum (FCS) 0.05% tween in PBS; 200 µl aliquot per well]. The plates were incubated at room temperature for 1.5 hr and subsequently washed 3 times in PBST (PBS with 0.05% tween). Mouse serum samples [diluted 1:3000 in PBST] were added in duplicates into the ovalbumin-coated wells (100 µl per well) and incubated at 37° C. for 1 hour. Following incubation, the plates were washed 3 times in PBST and then filled with an enzyme-conjugated antibody suspension [horseradish peroxidase-conjugated rabbit anti-mouse antibody (Jackson Immuno Research Laboratory INC, USA) diluted 1:5000 in blocking solution (10% FCS in PBST)]. The plates were incubated at 37° C. for 1 hr, washed five times in PBST, filled with 3,3',5,5'-tetramethylbenzidine peroxidase solution (Dako Corporation, CA, USA; 100 µl per well) and incubated at room temperature for sufficient time to allow enzymatic reaction (indicated by color formation). Following enzymatic reaction, the plates were filled with a stopping solution (0.18 M $H_2SO_4$; 100 µl per well) and analyzed for absorbance at 450 nm by a microplate reader (Dynex Technologies, MRX Chantilly, Va.).

Results:

As can be seen in FIG. 9, mice which had been fed ovalbumin-transformed red microalgae produced substantial amount of anti-ovalbumin antibody, while no immune response was observed in control mice which had been fed with wild-type algae.

Figure 10:
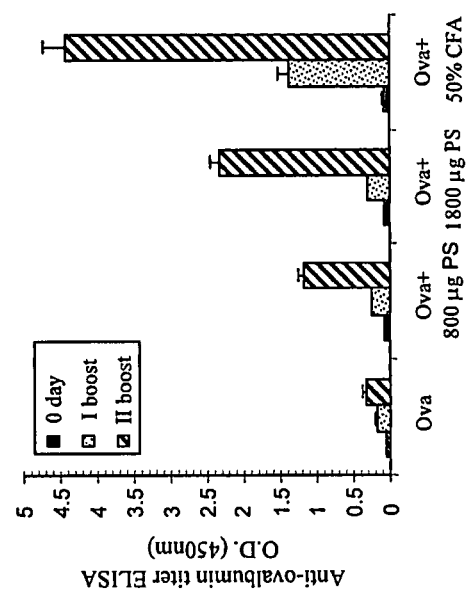
FIG. 10 is an ELISA analysis illustrating adjuvant effect of polysaccharide. Mice were injected subcutaneously with 50 μg of ovalbumin alone or mixed with polysaccharide (PS) or in complete Freund's adjuvant (CFA). The serum from each mouse was analyzed for antibodies against ovalbumin by the standard ELISA method.

In additional experiments, the cell wall polysaccharide of the red microalgae *Porphyridium* sp. was found to comprise adjuvant activity (FIG. 10), which may serve as a built-in adjuvant when using the red microalgae as an oral vaccine.

Example 6

Secretion of the Recombinant Hepatitis B S Antigen (HBsAg) from Transgenic Algae The ability of the algal cell-factory system to produce high levels of recombinant protein via secretion to the medium was demonstrated using the vaccine protein HBsAg.

Materials and Methods:

Algal transformation: Algal cells were co-transformed with the Zeocin-resistance plasmid and the HBsAg plasmid as described in Example 3.

DNA Extraction: DNA extraction was carried out as described in Example 4.

PCR analysis: HBsAg gene was amplified from DNA extracts by PCR using the primers set forth in SEQ ID NOs: 14-15 using the following PCR protocol: 3 cycles of: 95° C.—2 min, 60° C.—1 min, 72° C.—1 min, following by 30 cycles of: 95° C.—30 sec, 60° C.—45 sec, 72° C.—1 min, ending with 72° C.—5 min and cooling to 4° C.

Protein sample preparation: Media samples, containing secreted protein, were collected from $20 \times 10^6$ cells/ml logarithmic algal cultures after centrifugation for 10 min at 3,000 g.

Western blot analysis: The expression level of the foreign proteins in algal transformant media was tested using a standard Western blot immunoassay with the Rabbit Anti hepatitis B antibodies (Virostat, Portland Me. USA) in a 1:300 dilution. The Engerix B Yeast-derived, Hepatitis B Vaccine (S antigen) (GlaxoSmithKline Biologicals, Rixensart, Belgium) served as a control.

Figure 11:
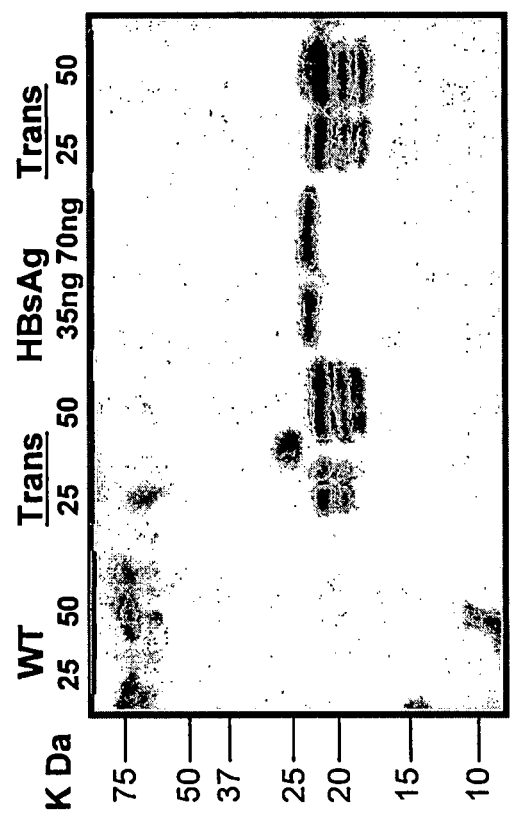
FIG. 11 is a Western blot analysis illustrating expression levels of secreted Hepatitis B small surface antigen (S antigen) from transgenic algae, obtained from the growth media of transformed *Porphyridium* sp. Specifically, 25 μl (lanes 1, 3 and 7) or 50 μl (lanes 2, 4 and 8) of growth media were analyzed, where the original concentration of algae cells was 20 million cells/ml. WT (wild-type) samples refer to growth media from control non transgenic algae (lanes 1 and 2). For reference and comparison 35 ng (lane 5) and 70 ng (lane 6) of pure S antigen were run on the same gel.

Results:

HBsAg gene expression: Secretion of HBsAg in transformed algae cultures was confirmed and quantified by Western blot analysis. As can be seen in FIG. 11, growth media samples from wild type (WT) and transgenic algae (25 and 50 µl) were separated on a protein gel and compared to pure S antigen (35 ng and 70 ng). Using specific rabbit anti Hepatitis B S antigen antibodies, the presence of recombinant HBsAg was revealed in the transgenic growth media but not in WT. The amount of the expressed protein was calculated by band intensity comparison to be approximately 2-3 mg per 1 liter culture. The slight difference in size between the control S antigen and the recombinant HBsAg is probably a result of a different glycosylation pattern in red microalgae as compared to the commercial yeast produced recombinant HBsAg.

Hence, it has been demonstrated that red microalgae can be used as host cells for high throughput, cost effective and safe production of transgenic pharmaceutical polypeptides. The recombinant polypeptides may be administered as part of the red microalgae so as to provide protective encapsulation for convenient and safe oral delivery. Alternatively, the recombinant polypeptides may be secreted into the cell media.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

REFERENCES CITED

Additional References are Cited Hereinabove

1. Arad (Malis), S., Dubinsky, O. and Simon, B. (1993). A modified cell wall mutant of the red microalga *Rhodella reticulata* resistant to the herbicide. DCB. *J. Phycol.* 29 309-313.
2. Birch, R. G. (1997). PLANT TRANSFORMATION: Problems and Strategies for Practical Application. *Annu. Rev. Plant Physiol. Plant Mol. Biol.* 48 297-326.
3. Bura-Halfon, S., Rise, M., (Malis) Arad, S, and Sivan, A. (1997). Characterization of mutants of the red microalga *Porphyridium aerugineum* (Rhodophyceae) resistant to DCMU and atrazine. *Phycologia.* 36 (6)479-487.
4. Craige, J. S. (1990). Cell Walls. Biology of the red algae 221-257

5. Garber, K. (2001). Biotech industry faces new bottleneck. *Nature Biotechnology.* 19 184-185.
6. Geresh, S. and Arad (Malis) S. (1991). The extracellular polysaccharides of the red microalgae: chemistry and rheology. Biores. Technol. 38 195-201.
7. Goeddel, D. V., Heyneker, H. L., Hozumi, T., Arentzen, R., K., I., Yansura, D. G., Ross, M. J., Miozzari, G., Crea, R. and Seeburg, P. H. (1979a). Direct expression in *Escherichia coli* of a DNA sequence coding for human growth hormone. *Nature.* 281 544-548.
8. Goeddel, D. V., Kleid, D. G., Bolivar, F., Heyneker, H. L., Yansura, D. G., Crea, R., Hirose, T., Kraszewski, A., Itakura, K. and Riggs, A. D. (1979b). Expression in *Escherichia coli* of chemically synthesized genes for human insulin. *Proc. Natl. Acad. Sci. USA.* 76 106-110.
9. Lapidot, M., Raveh, D., Sivan, A., Arad (Malis), S. and Shapira, M. (2002). Stable chloroplast transformation of the unicellular red alga *Porphyridium* sp. *Plant Physiology.* 129 7-12.
10. Martial, J. A., Hallewell, R. A., Baxter, J. D. and Goodman, H. M. (1979). Human growth hormone: complementary DNA cloning and expression in bacteria. Science. 205 602-607.
11. Patwary, M. U. and van der Meer J. P. (1994). Application of RAPD markers in an examination of heterosis in *Gelidium vagum* (Rhodophyta). *J. Phycol.* 30 91-97.
12. Sambrook, J., Fritsch, E. F. and Maniatis, T. (1989). *Molecular Cloning: A Laboratory Manual*, Cold Spring Harbor Laboratory Press.
13. Schillberg, S., Fischer, R. and Emans, N. (2003). "Molecular farming" of antibodies in plants. *Naturwissenschaften.* 90 145-155.
14. Simon, B., Geresh, S. and Arad (Malis), S. (1992). Degradation products of the cell wall polysaccharide of the red microalga *Porphyridium* sp. (Rhodophyta) by means of Enzymatic activity of its predator the dinoflagellate *Gymnodinium* sp. (Gymnodiales). *J. Phycol.* 28 460-465.
15. Simon-Bercovitch, B., Bar-Zvi, D. and Arad (Malis), S. (1999). Cell wall formation during the cell cycle of *Porphyridium* sp. (UTEX 637) Rhodophyta *J. Phycol.* 35(1): 78-83.
16. Sivan, A. and Arad (Malis), S. (1995). A mutant of the red microalga *Porphyridium* sp. (Rhodophyceae) resistant to DCMU and atrazine. *Phycologia.* 34 (4)299-305.
17. Van-Moppes, D., Barak, Z., Chipman, D. M., Gollop, N. and Arad (Malis), S. (1989). An herbicide (sulfometuron methyl) resistant mutant in *Porphyridium* (Rhodophyta). *J. Phycol.* 25 108-112.
18. Zhang, W., Subbarao S., Addae P., Shen A., Armstrong C., Peschke V. and Gilbertson L. (2003). Cre/lox-mediated marker gene excision in transgenic maize (*Zea mays* L.) plants. *TAG* 107 (7) 1157-1168.

What is claimed is:

1. A red microalga cell which expresses an exogenous protein which is secreted from the microalga cell, the red microalga cell being a *Porphyridium* cell.

2. The red microalga cell of claim 1, wherein said exogenous protein is a therapeutic or nutritive protein.

3. The red microalga cell of claim 1, wherein said cell is devoid of an exogenous antibiotic resistance gene.

* * * * *